(12) United States Patent
Yiu et al.

(10) Patent No.: US 9,411,931 B2
(45) Date of Patent: Aug. 9, 2016

(54) METHOD, APPARATUS AND COMPUTER PROGRAM PRODUCT FOR RECEIVING DIGITAL DATA FILES

(75) Inventors: Edwood Yiu, Vancouver (CA); Shirley Ma, Delta (CA); Lily Lai, Richmond (CA)

(73) Assignee: McKesson Financial Holdings, Hamilton (BM)

( * ) Notice: Subject to any disclaimer, the term of this patent is extended or adjusted under 35 U.S.C. 154(b) by 1019 days.

(21) Appl. No.: 13/354,912

(22) Filed: Jan. 20, 2012

(65) Prior Publication Data

US 2013/0191487 A1     Jul. 25, 2013

(51) Int. Cl.
*G06F 15/16*    (2006.01)
*G06F 19/00*    (2011.01)

(52) U.S. Cl.
CPC ................ *G06F 19/321* (2013.01)

(58) Field of Classification Search
CPC ...................................................... G06F 19/321
USPC ....................................................... 709/213
See application file for complete search history.

(56) References Cited

U.S. PATENT DOCUMENTS

| | | | |
|---|---|---|---|
| 6,553,141 B1 * | 4/2003 | Huffman | 382/232 |
| 6,574,629 B1 * | 6/2003 | Cooke et al. | |
| 6,711,297 B1 * | 3/2004 | Chang et al. | 382/240 |
| 6,891,920 B1 * | 5/2005 | Minyard et al. | 378/37 |
| 6,925,208 B1 * | 8/2005 | Huffman | 382/232 |
| 6,938,211 B1 * | 8/2005 | Chang et al. | 715/733 |
| 7,310,651 B2 * | 12/2007 | Dave et al. | 705/3 |
| 7,411,693 B2 * | 8/2008 | Loukipoudis et al. | 358/1.15 |
| 7,483,058 B1 * | 1/2009 | Frank et al. | 348/222.1 |
| 7,523,505 B2 * | 4/2009 | Menschik et al. | 726/26 |
| 7,574,452 B2 * | 8/2009 | Keen | |
| 7,583,861 B2 * | 9/2009 | Hanna et al. | 382/305 |
| 7,606,861 B2 * | 10/2009 | Killcommons et al. | 709/206 |
| 7,660,413 B2 * | 2/2010 | Partovi et al. | 380/33 |
| 7,698,366 B2 * | 4/2010 | Schofield et al. | 709/205 |
| 7,706,626 B2 * | 4/2010 | Heath et al. | 382/263 |
| 8,005,921 B2 * | 8/2011 | Ho et al. | 709/217 |
| 8,145,001 B2 * | 3/2012 | Khorasani et al. | 382/232 |
| 8,150,175 B2 * | 4/2012 | Natanzon et al. | 382/232 |
| 8,171,065 B2 * | 5/2012 | Slik et al. | 707/822 |
| 8,379,523 B2 * | 2/2013 | Gunatilake | 370/235 |

(Continued)

OTHER PUBLICATIONS

Clunie, D. et al. "Digital Imaging and Communications in Medicine (DICOM)—Application/DICOM MIME Sub-Type Registration," RFC 3240, Feb. 2002.*

(Continued)

*Primary Examiner* — Melvin H Pollack
(74) *Attorney, Agent, or Firm* — Alston & Bird LLP (57) ABSTRACT

A method, apparatus and computer program product are provided to efficiently receive digital imaging data files, regardless of their size. For a respective data packet of a digital imaging data file, the method may determine whether that portion of the digital imaging data file that has been received satisfies the first threshold. If the first threshold is not satisfied, the method may receive the respective data packet using memory, such as by appending the data packet to a linked list. However, if the first threshold is satisfied, the method may receive the respective data packet and subsequent data packet(s) of the digital imaging data file using file storage. The receipt of the respective data packet using file storage is slower than the receipt of the respective data packet using memory.

20 Claims, 3 Drawing Sheets

(56) References Cited

U.S. PATENT DOCUMENTS

| | | | |
|---|---|---|---|
| 8,384,729 B2* | 2/2013 | Niwa | 345/581 |
| 8,407,267 B2* | 3/2013 | Feulner et al. | 382/131 |
| 8,634,677 B2* | 1/2014 | Hu et al. | 382/305 |
| 8,867,807 B1* | 10/2014 | Fram | 382/128 |
| 8,898,267 B2* | 11/2014 | Slik et al. | 709/223 |
| 8,923,580 B2* | 12/2014 | Dekel et al. | 382/128 |
| 8,924,983 B2* | 12/2014 | Zhu et al. | 718/104 |
| 8,935,280 B2* | 1/2015 | Bauman et al. | 707/770 |
| 8,935,431 B2* | 1/2015 | Oehme et al. | 709/248 |
| 2001/0029520 A1* | 10/2001 | Miyazaki et al. | 709/200 |
| 2002/0016718 A1* | 2/2002 | Rothschild et al. | 705/2 |
| 2003/0117916 A1* | 6/2003 | Makela et al. | 369/53.2 |
| 2005/0001911 A1* | 1/2005 | Suzuki | 348/231.99 |
| 2006/0149601 A1* | 7/2006 | Langhofer et al. | 705/3 |
| 2006/0167945 A1* | 7/2006 | Trautner | 707/104.1 |
| 2006/0177114 A1* | 8/2006 | Tongdee et al. | 382/128 |
| 2007/0067278 A1* | 3/2007 | Borodziewicz et al. | 707/4 |
| 2008/0062270 A1* | 3/2008 | Lawson | 348/220.1 |
| 2010/0063842 A1* | 3/2010 | Carroll et al. | 705/3 |
| 2011/0110568 A1* | 5/2011 | Vesper et al. | 382/128 |
| 2012/0154654 A1* | 6/2012 | Li et al. | 348/302 |
| 2013/0060579 A1* | 3/2013 | Yu et al. | 705/3 |
| 2014/0328517 A1* | 11/2014 | Gluncic | 382/103 |
| 2014/0341450 A1* | 11/2014 | Sedan | 382/128 |
| 2015/0006612 A1* | 1/2015 | Natoli et al. | 709/202 |

OTHER PUBLICATIONS

Strickland, N. "PACS (Picture Archiving and Communication Systems): Filmless Radiology," Archives of Disease in Childhood, vol. 83, Issue 1, Jul. 2000, pp. 82-86.*

* cited by examiner

METHOD, APPARATUS AND COMPUTER PROGRAM PRODUCT FOR RECEIVING DIGITAL DATA FILES

TECHNOLOGICAL FIELD

Embodiments of the present invention relate generally to the receipt of digital data files and, more particularly, to the efficient receipt of digital data files of different sizes.

BACKGROUND

Medical imaging often includes creating images and/or video sequences of the human body or parts of the human body for clinical purposes such as examination, diagnosis and/or treatment. These images may be acquired by a number of different imaging modalities including, for example, ultrasound (US), magnetic resonance (MR), positron emission tomography (PET), computed tomography (CT), mammography (MG), digital radiology (DR), computed radiology (CR) or the like. In a number of example medical imaging workflows, such as in the case of a picture archiving and communication system (PACS), a digital image data file for a patient may include one or more acquired images of the patient along with information that may reside with or otherwise accompany the images. This information may include, for example, a study identifier (ID) as well as patient information such as the patient's name, demographics, medical record number or the like.

A PACS may permit the digital imaging data file to be viewed, such as for diagnostic purposes, and/or archived for subsequent viewing and/or processing. The digital imaging data files may be formatted in accordance with a Digital Imaging and Communications in Medicine (DICOM) file format so as to facilitate the capture, transfer and storage of the digital imaging data files. In this regard, the source of the digital imaging data file, such as any of the various imaging modalities, may transfer the digital imaging data file through a network to a PACS utilizing a predefined protocol, such as the DICOM C-STORE protocol. While the PACS may store the digital imaging data file for viewing and/or processing, the PACS may, in turn, belong to an enterprise archive, such as an enterprise image repository, to which multiple PACS systems transfer the digital imaging data files collected by the individual PACS utilizing, for example, the DICOM C-STORE protocol, for archival purposes. If desired, a PACS that is a member of the enterprise image repository may subsequently retrieve the digital imaging data file for viewing or other purposes.

The digital imaging data files that are captured by the various imaging modalities and archived by a PACS and/or an enterprise image repository may include relatively small data files, such as data files less than 1 MB, and large data files such as data files greater than 1 GB. As a result of the relatively frequent transfer and storage of digital imaging data files, a PACS system and/or an enterprise image repository desirably receives and stores both small and large digital imaging data files in an efficient manner.

One technique for receiving digital imaging data files involves the storage of the digital imaging data files first into a local memory device, such as physical memory, Before eventually saving the file to its final location in a file storage system. A digital imaging data file may be comprised of a plurality of data packets that may be received by a PACS or an enterprise image repository in a sequential fashion and the entire data file may initially be received using the local memory device, such as in a linked list within the local memory device. The direct receipt of the digital imaging data file using a local memory device is relatively quick and efficient. However, in instances in which the digital imaging data file is large, the local memory device may be exhausted with the PACS or the enterprise image repository being unable to allocate sufficient memory to receive the digital imaging data file, thereby resulting in a failure to receive the large data file. Additionally, as the local memory device may be utilized by a plurality of processes executed by the PACS or the enterprise image repository, the utilization of the local memory device and, in particular, the utilization of a substantial portion of the local memory device, in order to receive a large digital imaging data file, may limit or prevent access to the local memory device by other processes which may, in turn, be forced to utilize other, generally slower, storage techniques. In an instance in which a digital imaging file is received in physical memory, the digital imaging file may thereafter be saved to remote file storage following interpretation by the importing process.

Alternatively, a digital imaging data file may be received by the PACS or an enterprise image repository by immediately writing each data packet to file storage. In this regard, the file storage to which the data packets are written generally requires the transfer of the data packets across a network connection to the file storage. While the file storage may be substantially larger than the local memory device and, as such, may be able to receive substantially larger digital imaging data files, the process of writing each data packet to the file storage may be much slower since a separate input/output (I/O) operation is required for each data packet. While the additional time required to receive a digital imaging data file using file storage may be necessary in an instance which the digital imaging data file is large, the use of file storage in order to receive digital imaging data files is generally substantially slower than the use of a local memory device.

The challenges associated with efficiently receiving digital imaging data files are only exacerbated as a result of the formatting of the digital imaging data files in accordance with the DICOM format. In this regard, the DICOM format does not include an indication of the size of the file and, as such, the PACS and/or an enterprise image repository, may not be notified in advance, as to whether a digital imaging data file is large or small. Additionally, the challenges of efficiently receiving digital imaging data files appears to be increasing as larger digital imaging data files recently have become more common, and they are anticipated to become even more frequent in instances in which digital imaging data files are transferred from a PACS to an enterprise image repository.

BRIEF SUMMARY

A method, apparatus and computer program product are therefore provided in accordance with an example embodiment of the present invention in order to more efficiently receive digital imaging data files. In this regard, a method, apparatus and computer program product are provided in accordance with one embodiment in order to provide for improved efficiency with respect to the receipt of digital imaging data files that may be either relatively large or relatively small. For example, the method, apparatus and computer program produce of one example embodiment may strategically utilize both memory and file storage in order to receive digital imaging data files such that smaller digital imaging data files are received, at least initially with just memory while larger digital imaging files are received using a combination of memory and file storage.

In one embodiment, a method is provided that includes receiving a digital imaging data file comprised of a plurality of data packets. For example, the digital imaging data file may be received without an indication of the size of the digital imaging data file. For a respective data packet, the method determines whether that portion of the digital imaging data file that has been received satisfies the first threshold. In an instance in which the first threshold is not satisfied, the method may receive the respective data packet using memory, such as by appending the data packet to a linked list in the memory, such as for processing prior to transferring the digital image data file to remote file storage. However, in an instance in which the first threshold is satisfied, the method may receive the respective data packet and subsequent data packet(s) of the digital imaging data file using file storage, such as following transfer of data from the memory to the file storage. In this regard, the receipt of the respective data packet using file storage is slower than the receipt of the respective data packet using memory.

The method of one embodiment may also include, in an instance in which the first threshold is satisfied, initially receiving the respective data packet using a memory buffer. In this embodiment, the receipt of the respective data packet and subsequent data packet(s) using file storage may include the transfer of data from the memory buffer to the file storage in an instance in which the memory buffer contains data that satisfies the second threshold. The memory buffer may be sized to receive a plurality of data packets. As such, the transfer of data from the memory buffer may include performing a single input/output (I/O) operation in order to transfer the data comprising a plurality of data packets across a network connection to file storage. The receipt of a digital imaging data file may include the receipt of a plurality of digital imaging data files from a plurality of sources, such as a plurality of PACS. In this embodiment, the first and second thresholds associated with one source may differ from the first and second thresholds associated with another source.

In another embodiment, an apparatus is provided for receiving a digital imaging data file comprised of a plurality of data packets. The apparatus includes a memory, a file storage and a processor configured to determine, for a respective data packet, whether that portion of the digital imaging data file that has been received satisfies the first threshold. The processor is also configured, in an instance in which the first threshold is not satisfied, to receive the respective data packet using the memory, such as by appending the data packet to a linked list in the memory, such as for processing prior to transferring the digital image data file to remote file storage. The processor is further configured, in an instance in which the first threshold is satisfied, to receive the respective data packet and subsequent data packet(s) of the digital imaging data file using the file storage, such as following transfer of data from the memory to the file storage. The receipt of the respective data packet using the file storage is slower than receipt of a respective data packet using the memory.

The apparatus of one embodiment may also include a memory buffer. In this embodiment, the processor may be further configured, in an instance in which the first threshold is satisfied, to initially receive the respective data packet using the memory buffer. In accordance with this embodiment, the processor being configured to receive the respective data packet and subsequent data packet(s) using the file storage may include the processor being configured to transfer data from the memory buffer to the file storage in an instance in which the memory buffer contains data that satisfies the second threshold. The memory buffer may be sized to receive a plurality of data packets. As such, the processor being configured to transfer data may include the processor being configured to perform a single input/output (I/O) operation in order to transfer the data, including a plurality of data packets, across a network connection to the file storage. The processor of this embodiment may be configured to control receipt of a plurality of digital imaging data files from a plurality of sources, such as from a plurality of PACS. In this regard, the first and second thresholds associated with one source may differ from the first and second thresholds associated with another source. The digital imaging data file may be received without an indication of a size of the digital imaging data file.

In a further embodiment, a computer program product for storing a digital imaging data file comprised of a plurality of data packets is provided. The computer program product may include at least one non-transitory computer-readable storage medium having a computer-readable program instruction stored therein. The computer-readable program instructions may include program instructions configured, for a respective data packet, to determine whether that portion of the digital imaging file that has been received satisfies a first threshold. The computer-readable program instructions may also include program instructions configured, in an instance in which the first threshold is not satisfied, to receive the respective data packet using memory, such as by appending the data packet to a linked list in the memory, such as for processing prior to transferring the digital image data file to remote file storage. The computer-readable program instructions may also include program instructions configured, in an instance in which the first threshold that is satisfied, to receive the respective data packet and subsequent data packet(s) of the digital imaging data file using file storage, such as following transfer of data from the memory to the file storage. The receipt of the respective data packet using file storage is slower than the receipt of the respective data packet using the memory.

The computer program product of one embodiment also includes program instructions configured, in an instance in which the first threshold is satisfied, to initially receive the respective data packet using a memory buffer. In this regard, the program instructions configured to receive the respective data packet and subsequent data packet(s) using file storage may include program instructions configured to transfer data from the memory buffer to the file storage in an instance in which the memory buffer contains data that satisfies a second threshold. The memory buffer may be sized to receive a plurality of data packets. As such, the program instructions configured to transfer data may include program instructions configured to perform a single input/output (I/O) operation in order to transfer the data comprising a plurality of data packets across a network connection to the file storage. The computer-readable program instructions may also include program instructions configured to receive a plurality of digital imaging data files from a plurality of sources. In this regard, the first and second thresholds associated with one source may differ from the first and second thresholds associated with another source. The digital imaging data file may be received without indication of the size of the digital imaging data file.

BRIEF DESCRIPTION OF THE DRAWINGS

Having thus described the example embodiments of the present disclosure in general terms, reference will now be made to the accompanying drawings, which are not necessarily drawn to scale, and wherein:

DETAILED DESCRIPTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
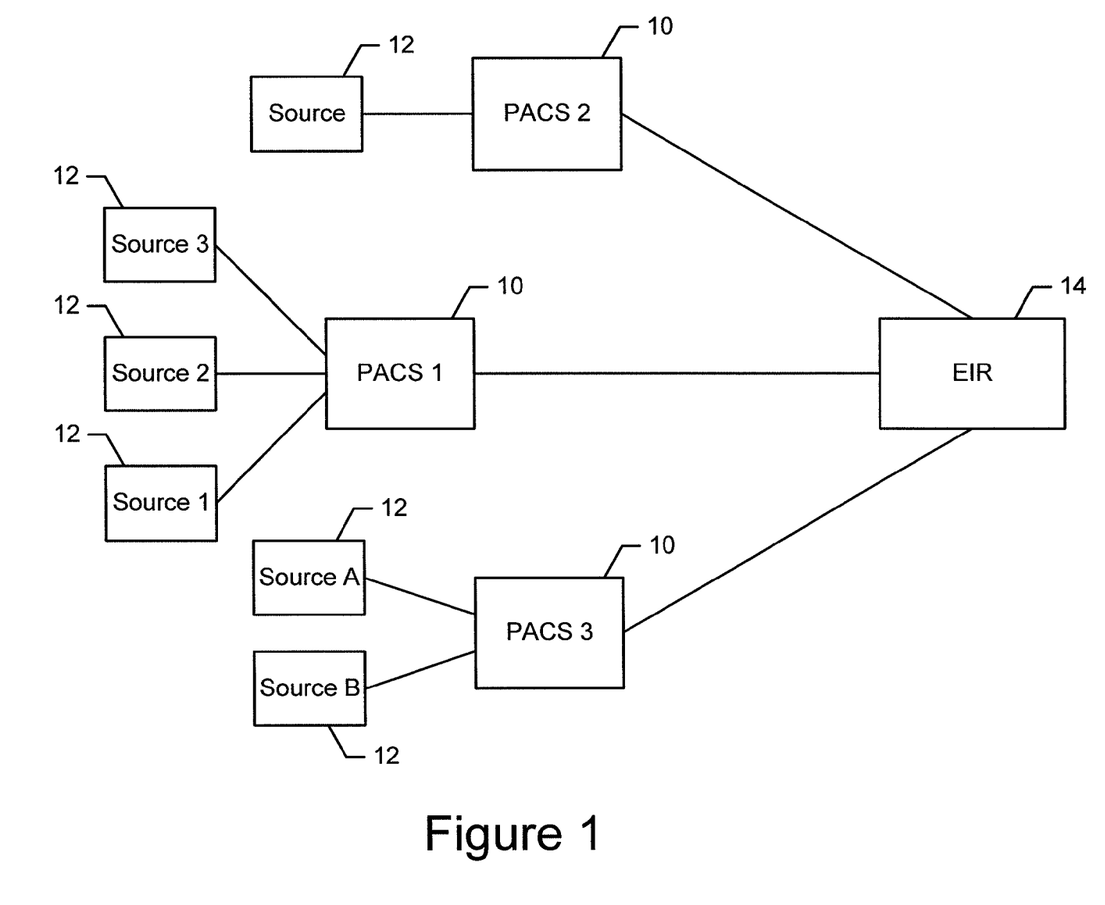
FIG. 1 is a schematic representation of a system in which an embodiment of the present invention may be implemented which includes a plurality of PACS and an enterprise imaging archive.

Referring now to FIG. 1, a system including one or more PACS 10 that may be configured in accordance with an example embodiment of the present invention is illustrated. A PACS may be configured to receive a digital imaging data file from a single source 12, that is, from a single imaging modality, such as US, MR, PET, CT, MG, DR, CR or the like. However, the PACS may alternatively be configured to receive digital imaging data files from a plurality of sources, such as from a plurality of imaging modalities. For purposes of example, the system of FIG. 1 includes three PACS, namely, PACS 1 that receives digital imaging data files from Source 1, Source 2 and Source 3, PACS 2 that receives digital imaging data files from a single source and PACS 3 that receives digital imaging data files from Source A and Source B.

A digital imaging data file may include one or more acquired images of the patient along with information that may reside with or otherwise accompany the images. This information may include, for example, an ID as well as patient information such as the patient's name, demographics, medical record number or the like. The digital imaging data file may be formatted in accordance with a predefined format, such as the DICOM format.

The PACS 10 may be an independent or standalone system as configured to communicate with one or more sources 12 in order to receive digital imaging data files. In this embodiment, the PACS may be solely responsible for storing the digital imaging data file, such as for subsequent viewing, processing or the like. In another embodiment, however, the PACS may belong to an enterprise system and, as such, may be in communication with an enterprise imaging repository (EIR) 14. In this regard, a plurality of PACS may be in communication with an enterprise imaging repository as shown in FIG. 1. As such, the enterprise imaging repository be configured to receive digital imaging data files from the PACS and to store the digital imaging data files. A PACS may subsequently recall or download a digital imaging data file that has been stored by the enterprise imaging repository so as to facilitate viewing and/or processing of the digital imaging data file by a user of the PACS. The digital imaging data files may be communicated between the various components of the system, such as between the sources and the PACS and between the PACS and the enterprise imaging repository in accordance with a predefined protocol, such as the DICOM C-STORE protocol.

As described above, the digital imaging data files may have varying sizes including larger digital imaging data files, such as digital imaging data files of 1 gigabyte (GB), 2 GB or larger, and small digital imaging data files, such as digital imaging data files of less than 1 megabyte (MB). As such, a method, apparatus and computer program product are provided according to one embodiment of the present invention for facilitating the efficient receipt of digital imaging data files regardless of the size of the digital imaging data file. In this regard, the receipt of a digital imaging data file includes the storage or saving of the digital imaging data file, sometimes only temporarily, such as for a limited period of time during which the file may be interpreted. In a system that includes a plurality of PACS 10 in communication with an enterprise archive repository 14, the enterprise archive repository may include or otherwise be associated with the method, apparatus or computer program product of an example embodiment of the present invention. Alternatively, in an instance in which a PACS is a standalone or independent PACS that is not supported by an enterprise archive repository, the PACS may include or otherwise be associated with the method, apparatus or computer program product of an example embodiment of the present invention. As therefore exemplified, the method, apparatus or computer program product of an embodiment of the present invention may be embodied by or associated with the system element that controls the receipt of the digital imaging data file.

Figure 2:
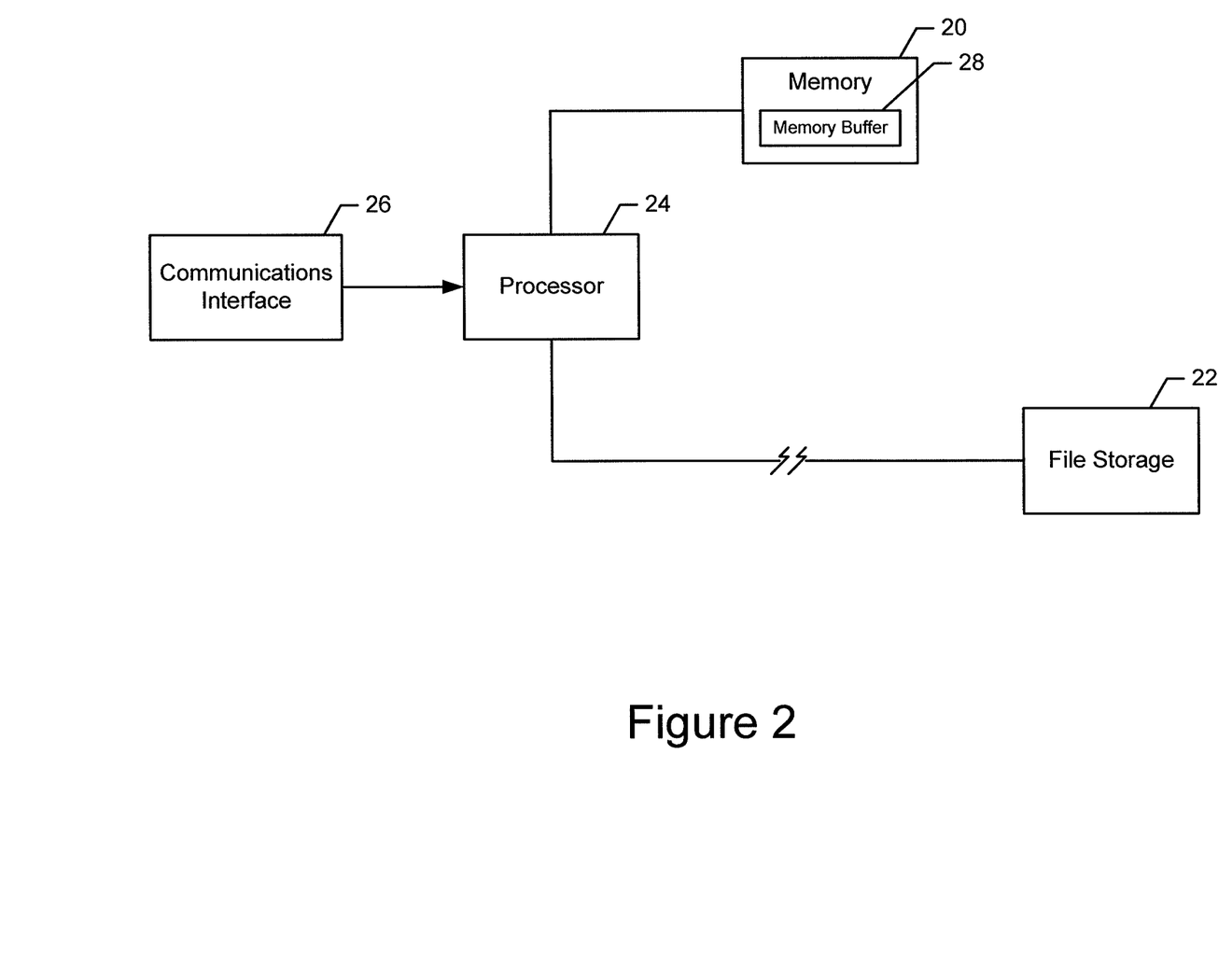
FIG. 2 is a block diagram of an apparatus that may be specifically configured in accordance with an example embodiment of the present invention.

Regardless of the instantiation of the method, apparatus or computer program product of an embodiment of the present invention, the apparatus of one embodiment of the present invention is shown in FIG. 2. The apparatus may include a memory 20, such as a local memory device, e.g., physical memory, such as random access memory (RAM). The apparatus also includes file storage 22. The file storage may be more remote than the memory and, in one embodiment may not be local, but may, instead, be remote so as to be accessible via a network connection, as represented by the broken line in FIG. 2. The file storage may be embodied in different manners, but in one embodiment, is EMC Centra file storage provided by EMC Corporation or the Hewlett Packard Medical Archiving Solution (MAS). Additionally, the apparatus may include a processor 24 for controlling the receipt of the digital imaging data file using the memory and/or the file storage.

The processor 24 may, for example, be embodied as one or more microprocessors, one or more coprocessors, one or more multi-core processors, one or more controllers, processing circuitry, one or more computers, various other processing elements including integrated circuits such as, for example, an ASIC (application specific integrated circuit) or FPGA (field programmable gate array), one or more other types of processors implemented in hardware, or some combination thereof. Accordingly, although illustrated in FIG. 2 as a single processor, in some embodiments the processor may comprise a plurality of processors. In some example embodiments, the processor is configured to execute instructions stored in a memory device, such as memory 20, an internal memory device or the like, or otherwise accessible to the processor. These instructions, when executed by the processor, may cause the apparatus to perform one or more of the functionalities as described herein. As such, whether configured by hardware or software methods, or by a combination thereof, the processor may comprise an entity capable of performing operations according to embodiments of the present invention while configured accordingly. Thus, for example, when the processor is embodied as an ASIC, FPGA or the like, the processor may comprise specifically configured hardware for conducting one or more operations described herein. Alternatively, as another example, when the processor is embodied as an executor of instructions, the instructions may specifically configure the processor to perform one or more algorithms and operations described herein.

Figure 3:
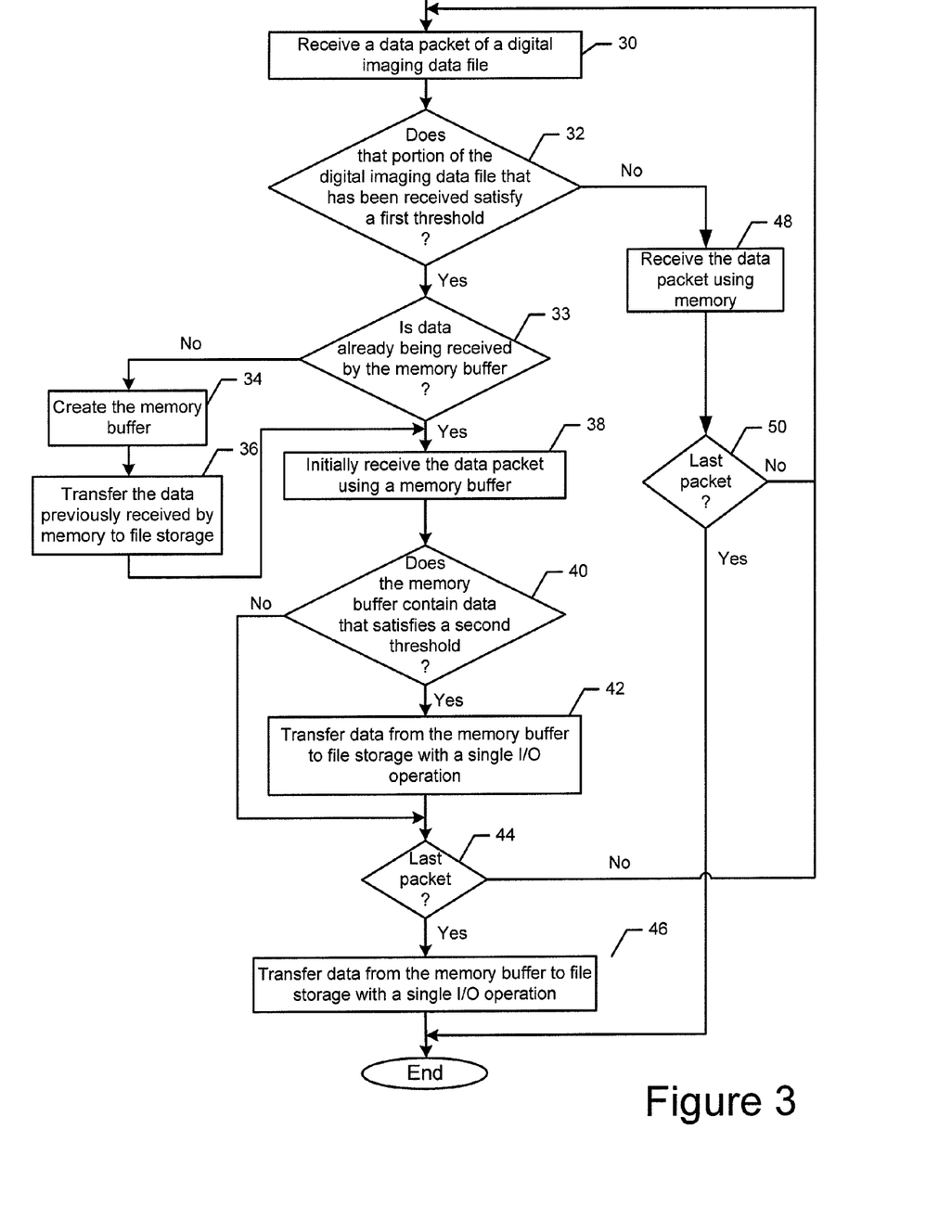
FIG. 3 is a flow chart illustrating operations performing in accordance with an embodiment of the present invention.

Referring now to FIG. 3 in which operations performed in accordance with an example embodiment to the present invention are illustrated, a digital imaging data file comprised of a plurality of data packets may be received, as shown in operation 30. While the processor 24 may directly receive the digital imaging data file, the apparatus of one embodiment may also include a communications interface 26 configured to receive the digital imaging data file and, in turn, to provide the digital imaging data file to the processor. The communication interface may be embodied as any device or means embodied in circuitry, hardware, a computer program product comprising a computer-readable medium (e.g. memory 22) storing computer-readable program instructions (e.g., software or firmware) that are executable by a suitably configured processing device (e.g., the processor), or a combination thereof that is configured to receive and/or transmit data from/ to another device, such as, for example, a source 12, a PACS 10 and/or the like. In some example embodiments, the communication interface is at least partially embodied as or otherwise controlled by the processor. In this regard, the communication interface may be in communication with the processor, such as via a bus. The communication interface may include, for example, an antenna, a transmitter, a receiver, a transceiver and/or supporting hardware or software for enabling communications.

The digital imaging data file may be received without an indication of the size of the digital imaging data file. For example, a digital imaging data file that is formatted in accordance with the DICOM format will not include an indication of the size of the digital imaging data file. Thus, the processor 24 may not be able to determine the size of the digital imaging data file while in the process of receiving the digital imaging data file, such as while receiving a sequence of data packets that comprise the digital imaging data file.

The digital imaging data file may be received from a respective source. In an embodiment to which a PACS 10 embodies or is otherwise associated with the apparatus of FIG. 2, the digital imaging data files may be received from one or more sources 12, such as one or more imaging modalities, including, for example, US, MR, PET, CT, MG, DR, CR or the like. Alternatively, in an embodiment in which the apparatus of FIG. 2 is embodied by an enterprise archive repository 14, the digital imaging data files may be received directly from any one of a plurality of PACS and indirectly from any one of a plurality of sources, such as imaging modalities, including those described above.

In accordance with an embodiment of the present invention, the processor 24 may be configured to receive at least an initial portion of each digital imaging data file using the memory 20. In instances in which a digital imaging data file is smaller than a first threshold, the processor may receive the entire digital imaging data file using the memory. Following receipt using memory, the digital imaging data file may be processed prior to transferring the digital imaging data file to file storage 22. In an instance in which the digital imaging data file has a size that is greater than the first threshold, however, the processor may be configured to receive an initial portion of the digital imaging data file up to the first threshold using the memory and to receive the remainder of the digital imaging data file using file storage 22. By utilizing the memory to receive all or at least a portion of each digital imaging data file prior to restoring to file storage, the receipt of the digital imaging data files may be made more efficient since the receipt of data packets using the memory is faster and more efficient than the receipt of data packets using file storage. However, by limiting the amount of the memory that may be utilized by a single digital imaging data file and by correspondingly causing a portion of the larger digital imaging data files to be received using file storage, the method, apparatus or computer program product of an example embodiment allow the memory to be utilized by a number of processes and to receive a number of digital imaging data files without being inequitably dominated by the receipt of a single, large digital imaging data file.

Moreover, in some embodiments as described below, the processor 24 may also utilize a memory buffer 28 to temporarily receive a plurality of data packets that are, in turn, to be stored in file storage 22. In this regard, the memory buffer may be an allocation of the memory 22 such that the memory buffer may be part of physical memory. As such, the processor may be configured to perform a single input/output (I/O) operation in order to transfer the data packets to the file storage following the accumulation of a plurality of data packets within the memory buffer, thereby limiting the number of I/O operations to be performed in order to receive the data packets using the file storage and correspondingly also increasing the efficiency with which data packets are received using the file storage.

By way of further explanation, reference is now made to operation 32 of FIG. 3 in which the processor 22, upon receipt of a respective data packet, determines whether that portion of the digital imaging data file that has been received satisfies a first threshold. That portion of the digital imaging data file that has been received includes the data packets of the same digital imaging data file that have been previously received. In one embodiment, that portion of the digital imaging data file that has been received includes the respective data packet, while in another embodiment, that portion of the digital imaging data file that has been received does not include the respective data packet. Regardless, the processor may compare the size, such as in bytes, of the portion of the digital imaging data file that has been received with the first threshold. The first threshold may be predefined, such as in a configuration file. The first threshold may be set to any desired value, but is generally set to a value that lies between the size of a small digital imaging data file and the size of a large digital imaging data file. For example, in an embodiment in which a distribution of the sizes of the digital imaging data files that will be received may be approximated, the first threshold may be established at a value such that a majority, e.g., at least 75%, at least 90%, etc., of the digital imaging data files will have a size that is less than the first threshold. The first threshold may also or alternatively be set to a value such that the allocation of a portion of the memory having a size equal to the value of the first threshold will not significantly impair the use of the memory by other processes. In one example, the first threshold may be 50 MB, but the threshold may have other values in other embodiments.

The first threshold may be satisfied in various manners. In one embodiment, however, the first threshold may be satisfied in an instance in which the processor 24 determines that that portion of the digital imaging data file that has been received has a size that equals or exceeds the first threshold.

As shown in operation 48 of FIG. 3, in an instance in which the processor 24 determines that the first threshold is not satisfied, the processor may be configured to receive the respective data packet using the memory 20. For example, the processor may be configured to append the data packet to a linked list in the memory. As shown in operation 50, the processor may then determine if the most recently received data packet was the last data packet of the digital imaging data file, such as may be indicated by a header, a flag or other information associated with the data packet, and, if so, may complete the process by which the digital imaging data file is received. However, in an instance in which the most recently received data packet was not the last data packet, the processor may prepare to receive the next data packet at operation 30.

However, in an instance in which the first threshold is satisfied, such as in an instance in which that portion of the digital imaging data file that has been received has a size that equals or exceeds the first threshold, the processor 24 may be configured to receive the respective data packet and any subsequent data packet(s) of the digital imaging data file using the file storage 22. By limiting the use of file storage to those instances in which the digital imaging data file exceeds a first threshold, the digital imaging data file may be more efficiently received since the receipt of the respective data packet using file storage is slower and less efficient than the receipt of the respective data packet using the memory.

While the processor 24 of one embodiment may be configured to immediately receive the respective data packet and each subsequent data packet of the digital imaging data file using file storage 22 in an instance in which the first threshold is satisfied, the processor of one embodiment may be configured to at least temporarily receive the respective data packet using a memory buffer 28. In this regard, the apparatus of FIG. 2 may also include a memory buffer that may be local to the processor and, as such, may provide for a relatively quick and efficient receipt of the respective data packet. In one embodiment, for example, the memory buffer may be a portion of the memory 20 itself. As shown in operation 33 of FIG. 3, the processor may be configured to determine if data packets are already being received by the memory buffer. If data packets are not already being received by the memory buffer, the processor may configure the memory 20 so as to allocate space for the memory buffer with the size of the memory buffer being defined, in one embodiment, to equal a second threshold. See operation 34 of FIG. 3. Additionally, the processor may cause any data that has been previously received in memory to be transferred to the file storage via a single I/O operation. See operation 36 of FIG. 3.

Once a memory buffer 28 has been created, the processor 24 may be configured to receive the respective data packet and one or more subsequent data packet(s) using the memory buffer and to transfer the data from the memory buffer to the file storage 22 in an instance in which the memory buffer contains data that satisfies a second threshold, such as by having a size that equals or exceeds the second threshold. See operations 38, 40 and 42 of FIG. 3. The second threshold may be predefined and, in one embodiment, may be defined in a configuration file along with the first threshold. The second threshold may be set to any of a variety of different values, but in one embodiment is predefined to a value that exceeds the size of the data packet and, more generally, exceeds the aggregate size of two or more data packets such that multiple data packets may be received in the memory buffer prior to transferring the data from the memory buffer to the file storage. For example, in an embodiment in which the data packet has size of 16 KB, the second threshold may have a value of 1 MB. However, the second threshold may have other values in other embodiments.

As described above, the memory buffer 28 may be sized to be at least as large as the value of the second threshold and, as such, may be sized to receive and store a plurality of data packets. In this embodiment, the transfer of the data from the memory buffer to the file storage 22 may include the performance, by the processor 24, of a single input/output (I/O) operation in order to transfer the data comprising the plurality of data packets stored in the memory buffer across a network connection to the file storage. By providing for the transfer of a plurality of data packets from the memory buffer to the file storage via a single I/O operation, as opposed to requiring a I/O operation for the transfer of each data packet, the method, apparatus, and computer program product of this example embodiment may further improve the efficiency of with which a digital imaging data file is received.

As shown in operation 44, the processor 24 may then determine if the most recently received data packet was the last data packet of the digital imaging data file and, if so, may complete the process of receiving the digital imaging data file. As shown in operation 46, in an instance in which the processor determines that the most recently received data packet was the last data packet of the digital imaging data file, the processor may transfer the data from the memory buffer 28 to file storage 22, such as via a single I/O operation, regardless of whether the data satisfies the second threshold. However, in an instance in which the most recently received data packet was not the last data packet, the processor may prepare to receive the next data packet at operation 30 prior to repeating the process of storing the data packet to file storage 22, either directly or via a memory buffer 28 as described above.

As noted above, digital imaging data files may be received from a plurality of sources 12. In order to permit the receipt of the digital imaging data files to be tailored based upon the source of the digital imaging data files, the first and second thresholds may be separately predefined for each source or, at least, each type of source, such as each different imaging modality. As such, the first and second thresholds associated with one source may differ from the first and second thresholds associated with another source. Accordingly, a source that is known to generally provide digital imaging data files of a certain size with an occasional, much larger digital imaging data file may cause the first threshold to be set to a value that exceeds the size of the majority of the digital imaging data files, but is less than the size of the occasional, much larger digital imaging data file.

By receiving at least a portion of each digital imaging data file in memory 20 and, indeed, by receiving the entirety of some and, in some instances, a majority of the digital imaging data files in memory prior to restoring the digital imaging data files to file storage 22 following processing of the digital imaging data files, the efficiency with which the digital imaging data files is received may be improved, while concurrently insuring that the memory is available for concurrent use by other processes. Additionally, by temporarily saving a plurality of data packets in a memory buffer 28 prior to transferring the plurality of data packets to file storage via a single input/output (I/O) operation, the method, apparatus and computer program product of an example embodiment of the present invention also improves the efficiency with which a digital imaging data file is received.

FIG. 3 illustrates a flowchart of a system, method, and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a PACS 10, an enterprise imaging repository 14 or other computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowcharts, and combinations of blocks in the flowcharts, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
    for a respective data packet of a digital imaging data file comprised of a plurality of data packets, determining, with a processor, whether that portion of the digital imaging data file that has been received equals or exceeds a first threshold defining a first file size;
    in an instance in which the first threshold is not satisfied in that the portion of the digital imaging data file that has been received has a size that is less than the first file size, receiving the respective data packet using a memory; and
    in an instance in which the first threshold is satisfied in that the portion of the digital imaging data file that has been received has a size that equals or exceeds the first file size, receiving the respective data packet and subsequent data packet(s) of the digital imaging data file using file storage, wherein receiving the respective data packet using file storage is slower than receiving the respective data packet using memory.

2. A method according to claim 1 further comprising, in an instance in which the first threshold is satisfied, initially receiving the respective data packet using a memory buffer, and wherein receiving the respective data packet and subsequent data packet(s) using file storage comprises transferring data from the memory buffer to the file storage in an instance in which the memory buffer contains data that satisfies a second threshold defining a second file size, smaller than the first file size.

3. A method according to claim 2 further comprising receiving a plurality of digital imaging data files from a plurality of sources, and wherein the first and second thresholds associated with one source differ from the first and second thresholds associated with another source.

4. A method according to claim 3 wherein receiving a plurality of digital data files comprises receiving a plurality of digital data files from a plurality of PACS.

5. A method according to claim 2 wherein the memory buffer is sized to receive a plurality of data packets, and wherein transferring data comprises performing a single input/output (I/O) operation in order to transfer the data comprising a plurality of data packets across a network connection to the file storage.

6. A method according to claim 1 further comprising receiving the digital imaging data file without indication of a size of the digital imaging data file.

7. A method according to claim 1 wherein receiving the respective data packet using memory comprises appending the data packet to a linked list in the memory.

8. An apparatus for storing a digital imaging data file comprised of a plurality of data packets, the apparatus comprising;
    a memory;
    a file storage; and
    a processor configured to determine, for a respective data packet, whether that portion of the digital imaging data file that has been received equals or exceeds a first threshold defining a first file size, said processor also configured, in an instance in which the first threshold is not satisfied in that the portion of the digital imaging data file that has been received has a size that is less than the first file size, to receive the respective data packet using the memory, said processor further configured, in an instance in which the first threshold is satisfied in that the portion of the digital imaging data file that has been received has a size that equals or exceeds the first file size, to receive the respective data packet and subsequent data packet(s) of the digital imaging data file using the file storage, wherein receipt of the respective data packet using the file storage is slower than receipt of the respective data packet using the memory.

9. An apparatus according to claim 8 further comprising a memory buffer, wherein the processor is further configured, in an instance in which the first threshold is satisfied, to initially receive the respective data packet using the memory buffer, and wherein the processor being configured to receive the respective data packet and subsequent data packet(s) in the file storage comprises the processor being configured to transfer data from the memory buffer to the file storage in an instance in which the memory buffer contains data that satisfies a second threshold defining a second file size, smaller than the first file size.

10. An apparatus according to claim 9 wherein the processor is configured to control receipt of a plurality of digital imaging data files from a plurality of sources, and wherein the first and second thresholds associated with one source differ from the first and second thresholds associated with another source.

11. An apparatus according to claim 10 wherein the plurality of digital data files comprise a plurality of digital data files from a plurality of PACS.

12. An apparatus according to claim 9 wherein the memory buffer is sized to receive a plurality of data packets, and wherein the processor being configured to transfer data comprises the processor being configured to perform a single input/output (I/O) operation in order to transfer the data comprising a plurality of data packets across a network connection to the file storage.

13. An apparatus according to claim 8 wherein the digital imaging data file is received without indication of a size of the digital imaging data file.

14. An apparatus according to claim 8 wherein the processor being configured to receive the respective data packet using memory comprises the processor being configured to append the data packet to a linked list in the memory.

15. A computer program product for storing a digital imaging data file comprised of a plurality of data packets, the computer program product comprising at least one non-transitory computer-readable storage medium having computer-readable program instructions stored therein, the computer-readable program instructions comprising:

program instructions configured, for a respective data packet, to determine whether that portion of the digital imaging data file that has been received equals or exceeds a first threshold defining a first file size;

program instructions configured, in an instance in which the first threshold is not satisfied in that the portion of the digital imaging data file that has been received has a size that is less than the first file size, to receive the respective data packet using memory; and program instructions configured, in an instance in which the first threshold is satisfied in that the portion of the digital imaging data file that has been received has a size that equals or exceeds the first file size, to receive the respective data packet and subsequent data packet(s) of the digital imaging data file using file storage, wherein receipt of the respective data packet using file storage is slower than receipt of the respective data packet using memory.

16. A computer program product according to claim 15 further comprising program instructions configured, in an instance in which the first threshold is satisfied, to initially receive the respective data packet using a memory buffer, and wherein the program instructions configured to receive the respective data packet and subsequent data packet(s) using file storage comprise program instructions configured to transfer data from the memory buffer to the file storage in an instance in which the memory buffer contains data that satisfies a second threshold defining a second file size, smaller than the first file size.

17. A computer program product according to claim 16 wherein the program instructions configured to receive a digital imaging data file comprise program instructions configured to receive a plurality of digital imaging data files from a plurality of sources, and wherein the first and second thresholds associated with one source differ from the first and second thresholds associated with another source.

18. A computer program product according to claim 16 wherein the memory buffer is sized to receive a plurality of data packets, and wherein the program instructions configured to transfer data comprise program instructions configured to perform a single input/output (I/O) operation in order to transfer the data comprising a plurality of data packets across a network connection to the file storage.

19. A computer program product according to claim 15 wherein the digital imaging data file is received without indication of a size of the digital imaging data file.

20. A computer program product according to claim 15 wherein the program instructions configured to receive the respective data packet using memory comprise program instructions configured to append the data packet to a linked list in the memory.

* * * * *